United States Patent [19]

Sommer et al.

[11] 4,246,418
[45] Jan. 20, 1981

[54] UNSYMMETRICAL BIS-QUATERNARY AMINO ACIDS

[75] Inventors: Harold Z. Sommer, Havre de Grace; George E. Wicks, Jr., Baltimore, both of Md.

[73] Assignee: The United States of America as represented by the Secretary of the Army, Washington, D.C.

[21] Appl. No.: 696,975

[22] Filed: Jan. 5, 1968

[51] Int. Cl.$^3$ ............................................. C07D 213/63
[52] U.S. Cl. .................................. 546/291; 424/263
[58] Field of Search ........................... 260/296, 482 C; 424/300, 263; 546/291

[56] References Cited

U.S. PATENT DOCUMENTS 3,188,955   6/1965   Brown ..................................... 102/24

Primary Examiner—Leland A. Sebastian

Attorney, Agent, or Firm—Nathan Edelberg; Robert P. Gibson

[57] ABSTRACT

New chemical compounds, bis-quaternary carbamates, having the generic formula:

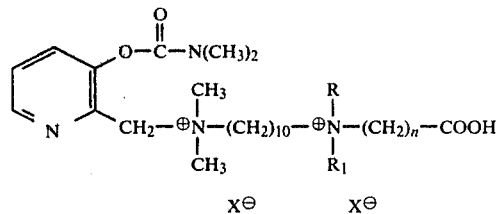

wherein R and $R_1$ are aliphatic radicals selected from the group consisting of methyl, ethyl, propyl, isopropyl, and butyl, wherein n is 1-9, wherein X is one equivalent of a monovalent or polyvalent anion, and having utility as toxic agents.

2 Claims, No Drawings

UNSYMMETRICAL BIS-QUATERNARY AMINO ACIDS

DEDICATORY CLAUSE

The invention described herein may be manufactured, used, and licensed by or for the Government for governmental purposes without the payment to us of any royalty thereon.

This invention relates to the synthesis of new toxic chemical compounds which are useful as chemical warfare agents. More particularly, our invention is concerned with novel compounds produced by means of a quaternizing reaction.

The chemical agents act mostly on the peripheral cholinergic nervous system which includes the motor nerves, the preganglionic fibers, the ganglia, the post-ganglionic parasympathetic fibers, and neuromuscular functions. The transmission of impulses along a nerve or from nerve fibers to muscle fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers they are attracted by anionic sites in animal tissues, particularly those situated at cell surfaces and interfaces. They can induce physiological responses that mimic or antagonize the action of acetylcholine as a result of their interaction with the various physiological receptor sites of acetylcholine, especially those at membranes of muscle cells. They also combine with enzymes such as acetylcholinesterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessibility of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the ease or difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influences association and hydration and may considerably change the solubilities in physiological media. In bis-quaternary and poly-quaternary compounds the distance between the electric charges must be considered. These factors contribute to govern the rate and reversibility of the chemical reactions involved, and contribute to determine the final physiological responses.

Our chemical agents interfere with the normal process of neuromuscular impulse transmission and thus disrupt the propagation of impulses from nerves to muscles. We have also found these compounds to be extremely toxic at relatively low dose levels in various animals.

The object of this invention is to synthesize new lethal agents useful in chemical warfare in high yields, said agents being well suited for industrial scale manufacture.

Other objects of and uses for the invention will in part be obvious and will in part appear hereinafter in the following detailed description thereof.

Our compounds may be employed in any munition suitable for handling a relatively non-volatile toxic agent such as bombs, shells, spray tanks, rockets, missiles, aerosol generators, and others.

In accordance with our invention, the tertiary amino-function of an aminoacid such as N,N-dimethylglycine was quaternized with N-(10-bromodecyl)-N-(3-dimethylcarbamoxy-α-picolyl)-N,N-dimethylammonium bromide, in a solvent mixture such as methanol and acetonitrile, under reflux conditions for a relatively prolonged period of time. The solvent mixture was evaporated under reduced pressure and the gummy residue stirred in a solvent such as acetonitrile. The unreacted aminoacid solidified and was removed by filtration. The filtrate was concentrated and upon addition of a solvent such as ethyl acetate an oily material separated. The supernatant solvent was decanted and the oily residue was stirred in a solvent such as acetone. The solvent was again decanted and the remaining gummy material was dissolved in a solvent such as acetonitrile. The solution was treated with decolorizing carbon and concentrated to a few milliliters. The addition of a solvent such as ethyl acetate caused a gummy material to separate. After triturating the gum in this solvent for a few minutes, the solvent was decanted and a solvent such as ether added. The mixture was allowed to stand at room temperature for a few days during which time partial solidification occurred. The solvent was evaporated and the residue dried in an apparatus that was kept under reduced pressure. The resultant white crystalline material constitutes the new compounds of the present invention which may be represented by the following generic formula:

$$\begin{array}{c} O \\ \| \\ O-C-N(CH_3)_2 \end{array}$$

$$CH_2-\overset{\oplus}{\underset{CH_3}{\overset{CH_3}{N}}}-(CH_2)_{10}-\overset{\oplus}{\underset{R_1}{\overset{R}{N}}}-(CH_2)_n-COOH$$

$$X^\ominus \qquad X^\ominus$$

wherein R and $R_1$ are aliphatic radicals selected from the group consisting of methyl, ethyl, propyl, isopropyl, and butyl, wherein n is 1–9 and wherein X is one equivalent of a monovalent or polyvalent anion.

The procedure used for the preparation of the new toxic materials is schematically shown below:

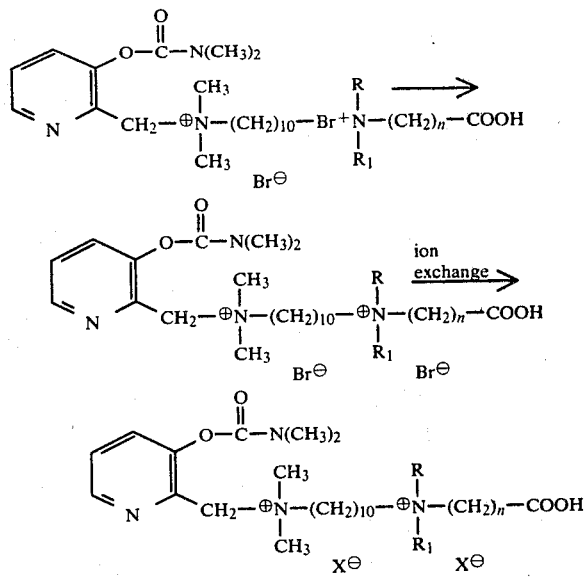

wherein X is a halide ion, preferably bromide, and R, R₁, and n as defined above.

If compounds are desired in which X is other than a halide ion, the above quaternary compounds are treated with the desired acid by simple exchange reactions as set forth below.

EXAMPLE

N-(10-Bromodecyl)-N-(3-dimethylcarbamoxy-α-picolyl)-N,N-dimethylammonium bromide (1.6 g) and N,N-dimethylglycine (0.62 g) were dissolved in 10 ml of methanol-acetronitrile (1:1) and the solution refluxed for 80 hours. The solvent mixture was evaporated under reduced pressure and the gummy residue was stirred in about 50 ml of acetonitrile. The unreacted N,N-dimethylglycine (0.3 g) solidified and was removed by filtration. The filtrate was concentrated to about 5 milliliters and the addition of about 50 ml of ethyl acetate caused an oily material to separate. The supernatant solvent mixture was decanted and the remaining viscous oily material stirred in about 50 ml of acetone. The acetone was decanted and the remaining gummy material dissolved in about 30 ml of acetonitrile. This solution was treated with decolorizing carbon and then concentrated to about 5 milliliters. About 50 ml of ethyl acetate was added causing a gummy material to precipitate. After triturating this gum in the solvent for a few minutes, the ethyl acetate was decanted, and about 30 ml of ether added. The mixture was allowed to stand at room temperature for 5 days during which time partial solidification occurred. The ether was evaporated and the semisolid was placed in an apparatus that was kept under reduced pressure (0.5 mm) for about 24 hours. The product, 1-[N-(3-dimethylcarbamoxy-α-picolyl)-N,N-dimethylammonio]-10(N-carbamoxymethyl-N,N-dimethylammonio)decane dibromide (0.7 g) was obtained as a white crystalline deliquescent material.

Analysis for $C_{25}H_{46}Br_2N_4O_4$. Calcd: C, 47.9; H, 7.4; N, 8.9; Br, 25.5. Found: C, 47.5; H, 7.2; N, 8.7; Br, 25.1.

| Toxicity IV $LD_{50}$ | |
|---|---|
| Rabbits | Mice |
| 0.017 mg/kg | 0.032 mg/kg |

Method of Preparation of N-(10-bromodecyl)-N-(3-dimethylcarbamoxy-α-picolyl)-N,N-dimethylammonium bromide.

A solution of 62.3 g of 2-dimethylaminomethyl-3-dimethylcarbamoxy-pyridine and 251 g of 1,10 dibromodecane was refluxed for about 7 days in about 1 liter of anhydrous ether. The product that formed was collected on a filter, washed with two 100 ml portions of anhydrous ether, and dissolved in about 1 liter of acetone. The acetone solution was treated with decolorizing carbon and filtered. The filtrate was concentrated under reduced pressure to approximately 200 ml. Ether was added until the solution became turbid. The mixture was then seeded and chilled overnight. The resultant crystalline product was collected and further purified by recrystallization from ethyl acetate. The pure product was dried in vacuo for 2 hours, yielding 76 g of material, m.p. 90° to 92° C.

Analysis for $C_{21}H_{37}Br_2N_3O_2$. Calcd: C, 48.2; H, 7.1; $Br^-$(ionic), 15.3; O, 6.1. Found: C, 48.2; H, 7.0; $Br^-$(ionic), 15.2; O, 6.2.

The compounds that are representative of our invention are listed below by name and chemical structure.

1-[N-(3-dimethylcarbamoxy-α-picolyl)-N,N-dimethylammonio]-10-(N-carboxymethyl-N,N-dimethylammonio)decane dibromide.

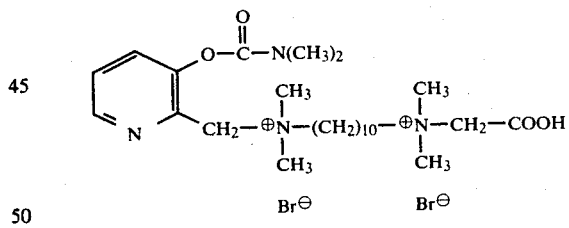

1-[N-(3-dimethylcarbamoxy-α-picolyl)-N,N-dimethylammonio]-10-(N-carboxymethyl-N,N-diethylammonio)decane dibromide.

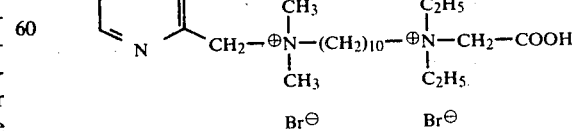

1-[N-(3-dimethylcarbamoxy-α-picolyl)-N,N-dimethylammonio]-10-(N-carboxymethyl-N-methyl-N-propylammonio)decane dibromide.

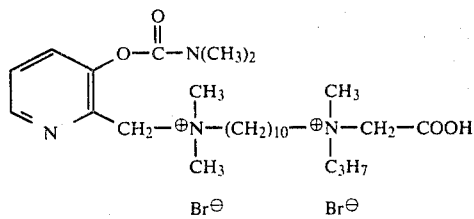

1-[N-(3-dimethylcarbamoxy-α-picolyl)-N,N-dimethylammonio]-10-(N-carboxymethyl-N-isopropyl-N-methylammonio)decane dibromide.

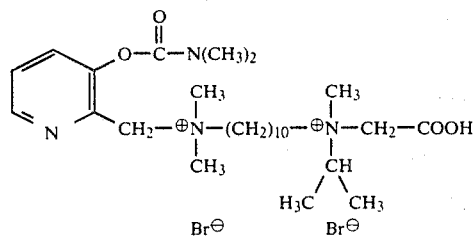

1-[N-(3-dimethylcarbamoxy-α-picolyl)-N,N-dimethylammonio]-10-(N-carboxymethyl-N-butyl-N-methylammonio)decane dibromide.

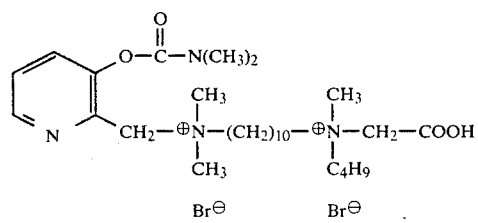

1-[N-(3-dimethylcarbamoxy-α-picolyl)-N,N-dimethylammonio]-10-[N-(2-carboxyethyl)-N,N-dimethylammonio]decane dibromide.

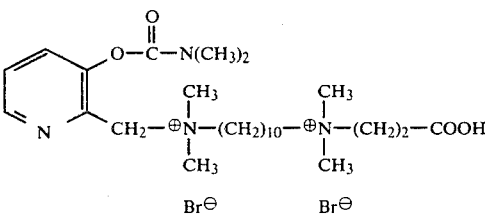

1-[N-(3-dimethylcarbamoxy-α-picolyl)-N,N-dimethylammonio]-10-[N-(3-carboxypropyl)-N,N-dimethylammonio]decane dibromide.

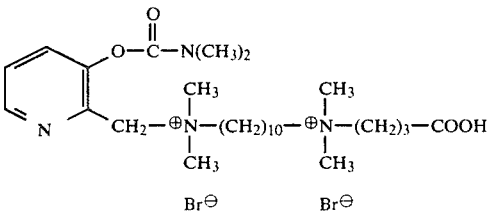

1-[N-(3-dimethylcarbamoxy-α-picolyl)-N,N-dimethylammonio]-10-[N-(4-carboxybutyl)-N,N-dimethylammonio]decane dibromide.

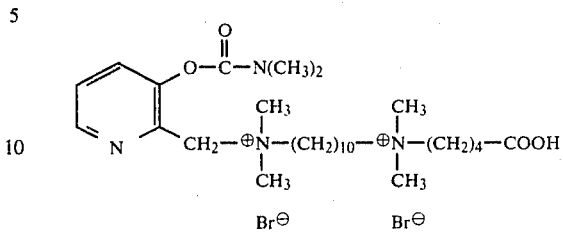

1-[N-(3-dimethylcarbamoxy-α-picolyl)-N,N-dimethylammonio]-10-[N-(6-carboxyhexyl)-N,N-dimethylammonio]decane dibromide.

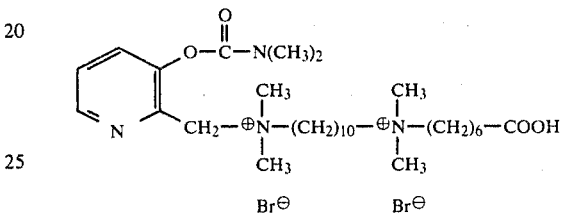

1-[N-(3-dimethylcarbamoxy-α-picolyl)-N,N-dimethylammonio]-10-[N-(9-carboxynonyl)-N,N-dimethylammonio]decane dibromide.

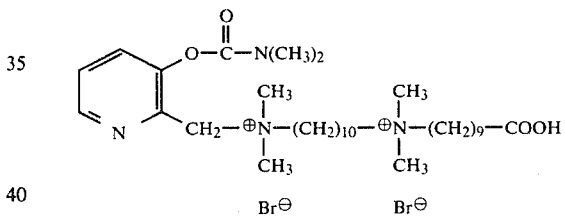

We have shown preferred compounds in which the anion is limited to the halogen moiety, in particular the bromide, since the bromoalkanes are good quaternizing agents. In general, however, it is only necessary that the anions merely have to meet the requirement of being capable of forming a stable salt with the quaternary nitrogen. Thus the halogen ions can be exchanged with other anions of relatively strong monovalent or polyvalent acid by conventional methods. For example, if $X^-$ is a bromide in the final product, a solution of the compound can be treated with a basic ion exchange resin or mixed with silver oxide and subsequently the desired acid is added to the quaternary hydroxide solution. Anions other than the halogens may also be obtained by metathesis with the halide form of the quaternary ammonium compound. Suitable as representations of $X^-$ are the anions hydrogen oxalate, perchlorate, nitrate, tetraphenylboronate, hydrogen sulfate. Representative examples of these additional end products are:

1-[N-(3-dimethylcarbamoxy-α-picolyl)-N,N-dimethylammonio]-10-(N-carboxymethyl-N,N-dimethylammonio)decane di(hydrogen oxalate);

1-[N-(3-dimethylcarbamoxy-α-picolyl)-N,N-dimethylammonio]-10-(N-carboxymethyl-N,N-dimethylammonio)decane diperchlorate;

1-[N-(3-dimethylcarbamoxy-α-picolyl)-N,N-dimethylammonio]-10-(N-carboxymethyl-N,N-dimethylammonio)decane dinitrate;

1-[N-(3-dimethylcarbamoxy-α-picolyl)-N,N-dimethylammonio]-10-(N-carboxymethyl-N,N-dimethylammonio)decane di(tetraphenylboronate);

1-[N-(3-dimethylcarbamoxy-α-picolyl)-N,N-dimethylammonio]-10-(N-carboxymethyl-N,N-dimethylammonio)decane di(hydrogen sulfate).

We claim:

1. New chemical compounds having the generic formula:

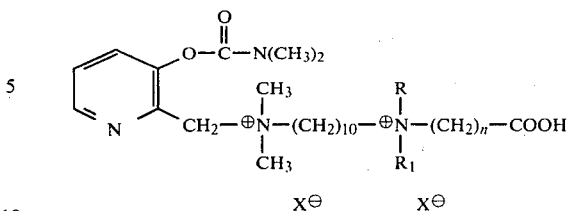

wherein R and R₁ are aliphatic radicals selected from the group consisting of methyl, ethyl, propyl, isopropyl, and butyl, wherein n is selected from 1–9, and wherein X is one equivalent of an anion selected from monovalent and polyvalent anions, said anions being selected from the group consisting of halide, hydrogen oxalate, perchlorate, hydrogen sulfate, nitrate, and tetraphenylboronate.

2. New chemical compounds selected from the group of compounds having the names:
1-[N-(3-dimethylcarbamoxy-α-picolyl)-N,N-dimethylammonio]-10-(N-carboxymethyl-N,N-dimethylammonio)decane dibromide;
1-[N-(3-dimethylcarbamoxy-α-picolyl)-N,N-dimethylammonio]-10-[N-(2-carboxymethyl)-N,N-dimethylammonio]decane dibromide; and
1-[N-(3-dimethylcarbamoxy-α-picolyl)-N,N-dimethylammonio]-10-[N-(3-carboxuypropyl)-N,N-dimethylammonio]decane dibromide.

* * * * *